(12) United States Patent
Van Agthoven et al.

(10) Patent No.: US 7,678,578 B2
(45) Date of Patent: *Mar. 16, 2010

(54) CELL PERMEABILIZATION AND STABILIZATION REAGENT AND METHOD OF USE

(75) Inventors: Andreas Van Agthoven, Marseilles (FR); Fabrice Malergue, Marseilles (FR); Enrique Rabellino, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 11/052,269

(22) Filed: Feb. 7, 2005

(65) Prior Publication Data

US 2006/0178294 A1 Aug. 10, 2006

(51) Int. Cl.
*G01N 33/72* (2006.01)
(52) U.S. Cl. .......................... 436/66; 436/17
(58) Field of Classification Search ............... None
See application file for complete search history.

(56) References Cited

U.S. PATENT DOCUMENTS

| | | | | |
|---|---|---|---|---|
| 4,477,438 | A * | 10/1984 | Willcockson et al. | 424/616 |
| 4,545,979 | A * | 10/1985 | Ambike et al. | 424/52 |
| 4,727,036 | A | 2/1988 | Knowles et al. | |
| 5,268,292 | A * | 12/1993 | Robertson et al. | 435/239 |
| 5,386,043 | A * | 1/1995 | Crudden | 554/68 |
| 5,747,343 | A * | 5/1998 | Tsuchiya et al. | 436/63 |
| 5,891,733 | A * | 4/1999 | Inoue | 436/63 |
| 6,060,322 | A | 5/2000 | Horton et al. | |
| 6,211,238 | B1 * | 4/2001 | Castillo et al. | 514/563 |
| 6,228,652 | B1 | 5/2001 | Rodriguez et al. | |
| 6,271,035 | B1 | 8/2001 | Deka et al. | |
| 6,413,921 | B1 * | 7/2002 | Childers et al. | 510/131 |
| RE37,891 | E * | 10/2002 | Collins et al. | 435/6 |
| 6,579,688 | B2 * | 6/2003 | Steaffens et al. | 435/7.92 |
| 6,958,244 | B2 | 10/2005 | Dotsch et al. | |
| 2004/0018586 | A1 * | 1/2004 | Rosendahl et al. | 435/68.1 |
| 2004/0185447 | A1 | 9/2004 | Maples et al. | |
| 2004/0214243 | A1 | 10/2004 | Burshteyn et al. | |

FOREIGN PATENT DOCUMENTS

| | | |
|---|---|---|
| EP | 0444240 B1 | 6/1996 |
| EP | 0617281 B1 | 6/1999 |
| WO | WO 88/07683 * | 10/1988 |

OTHER PUBLICATIONS

Zhang et al., 2002, Anal. Chem., 74:1729-1736.*
WO 03/096023,Jackson et al., 2003, 40 total pages.*
ChemExper Chemical Directory (retrieved from http://www.chemexper.com/chemicals/supplier/cas/97-78-9.html on Mar. 5, 2009 2 pages).*
Hampshire Hamposyl Surfactants (product brochure dated May 2000 (see last page) currently accessible from http://www.dewolfchem.com/pdf/Chattem_Personal_Care_Brochure.pdf 36 pages).*
MP Biomedicals (retrieved http://www.mpbio.com/product_info.php?products_id=190289 on Mar. 5, 2009 3 pages).*
Lach-Trifilieff, et al., "Complement Receptor 1 (CD35) on Human Reticulocytes: Normal Expression in Systemic Lupus Erythematosus and HIV-Infected Patients", The Journal of Immunology, 162, 7549-7554 (1999).
SmartMeasurement, Inc. [online]. Fluid Conductivity, Conductivity of Common Fluids (pp. 1-6), Copyright 2001-2002 [retrieved on Oct. 25, 2007]. Retrieved from the Internet: <http://www.smartmeasurement.com/en/wizards/flowmeter/flmtr_mag_conductivity.asp> See p. 3, "Hydrogen Peroxide".

* cited by examiner

*Primary Examiner*—Anish Gupta
*Assistant Examiner*—Ronald T Niebauer
(74) *Attorney, Agent, or Firm*—Cuspa Technology Law Associates; Mitchell E. Alter

(57) ABSTRACT

A cell permeabilization and stabilization reagent and method of use are disclosed. The reagent contains a N-acyl sarcosine or a salt thereof, a pH adjusting agent to adjust pH of the reagent in a range from about 4 to about 6; and an aqueous medium; the reagent having a low ionic strength defined by a conductivity of less than 9.0 mS/cm. The reagent further contains bovine serum albumin and glycerol. The reagent may further include an alkyl sulfate surfactant. Upon incubating the cells with the reagent, the reagent permeates the cellular membrane to allow penetration of an intracellular marker, causes intracellular protein aggregation within the cellular membrane, while preserves a cellular constituent for binding with a cellular marker for subsequent analysis by flow cytometry.

12 Claims, 5 Drawing Sheets

CELL PERMEABILIZATION AND STABILIZATION REAGENT AND METHOD OF USE

FIELD OF THE INVENTION

The present invention relates to a cell permeabilization and stabilization reagent and the method of use for preparing a sample containing cells for analysis of cellular constituents.

BACKGROUND OF THE INVENTION

Analysis of the cell interior at molecular level is the subject of growing interest. Several probes and antibodies have recently appeared which are used in research as well as routinely and are directed against intracellular structures. These probes and antibodies, because of their macromolecular character, cannot penetrate into the cell through the cellular membrane by themselves. Treatment of the cells is therefore necessary to render the cellular membrane permeable (permeabilization stage). This treatment causes an important modification of the exterior lipid membrane and can, depending on the method used, lead to a loss of the cell morphology, or even a loss of the entire cell.

A standard permeabilization method consists of a treatment of the cells on a microscope slide or in suspension, with dilutions of alcohols at low temperature (−20° C.). This method has the advantage that the molecular structures and the intracellular target antigens are well preserved. But in addition to the complicated procedure, and the low temperature used, the cell morphology is substantially modified at the end of treatment.

Several permeabilization methods use a fixation of the cells by chemical modification of the proteins using aliphatic aldehydes leading to cross-linking and aggregation of the proteins. The permeabilization is obtained by a treatment with an alcohol or a surfactant. The fixation by aliphatic aldehydes is especially known for its good preservation of the cell morphology after permeabilization. However, at protein molecular level, many antigen sites are destroyed by the fixation methods.

Reagents for permeabilizing the cells are more commonly found in the groups of organic solvents, alcohols, weak bases and weak acids. These reagents permeabilize the cellular membrane, however they do not generally stabilize the cell morphology.

It is therefore desirable to have a reagent for permeabilization of cells, which protects the cell morphology after permeabilization and does not modify the antigen sites inside and outside the cell.

SUMMARY OF THE INVENTION

In one embodiment, the present invention is directed to a cell permeabilization and stabilization reagent, which comprises a N-acyl sarcosine or a salt thereof represented by following molecular structure: $R_1$—CO—N(CH$_3$)CH$_2$COOX$_1$, wherein $R_1$ is an alkyl or alkylene group having 8 to 18 carbon atoms, and $X_1$ is H, Na$^+$, or K$^+$; a pH adjusting agent to adjust pH of said reagent less than 7; and an aqueous medium. The reagent has a low ionic strength defined by a conductivity of less than 9.0 mS/cm. Preferably, the N-acyl sarcosine is N-lauroyl sarcosine or a salt thereof, the pH of the reagent is in a range from about 4 to 6, and the conductivity of less than 1.2 mS/cm.

Preferably, the permeabilization and stabilization reagent further comprises bovine serum albumin and glycerol to enhance permeability of the cellular membrane and to stabilize the surfactant.

Optionally, the permeabilization and stabilization reagent can further comprise an anionic surfactant represented by following molecular structure: $R_2$—O—SO$_3$X$_2$; wherein $R_2$ is an alkyl or alkylene group having 8 to 18 carbon atoms; and $X_2$ is Na$^+$, K$^+$, NH$_4^+$ or NH$_2$C(CH$_2$OH)$_3$. Preferably, the anionic surfactant is Tris lauryl sulfate.

In a further embodiment, the present invention is directed to a method of permeating cellular membrane and preserving cellular constituents of a cell for flow cytometry analysis. The method comprises steps of mixing a sample containing cells with the cell permeabilization and stabilization reagent to form a sample mixture; and incubating the sample mixture for a period of time sufficient to permeate cellular membrane, and cause intracellular protein aggregation within the cellular membrane, while preserve a cellular constituent for binding with a cellular marker; adding a cellular marker into the sample mixture, and incubating the sample mixture for a further period of time to allow the cellular marker to bind with the preserved cellular constituent. The method can further comprise fixing the cells after the cellular marker binds to the cellular constituent in the sample mixture. The sample mixture can be analyzed on a flow cytometric instrument by light scatter and fluorescence analyses.

DETAILED DESCRIPTION OF THE INVENTION

Figure 1:
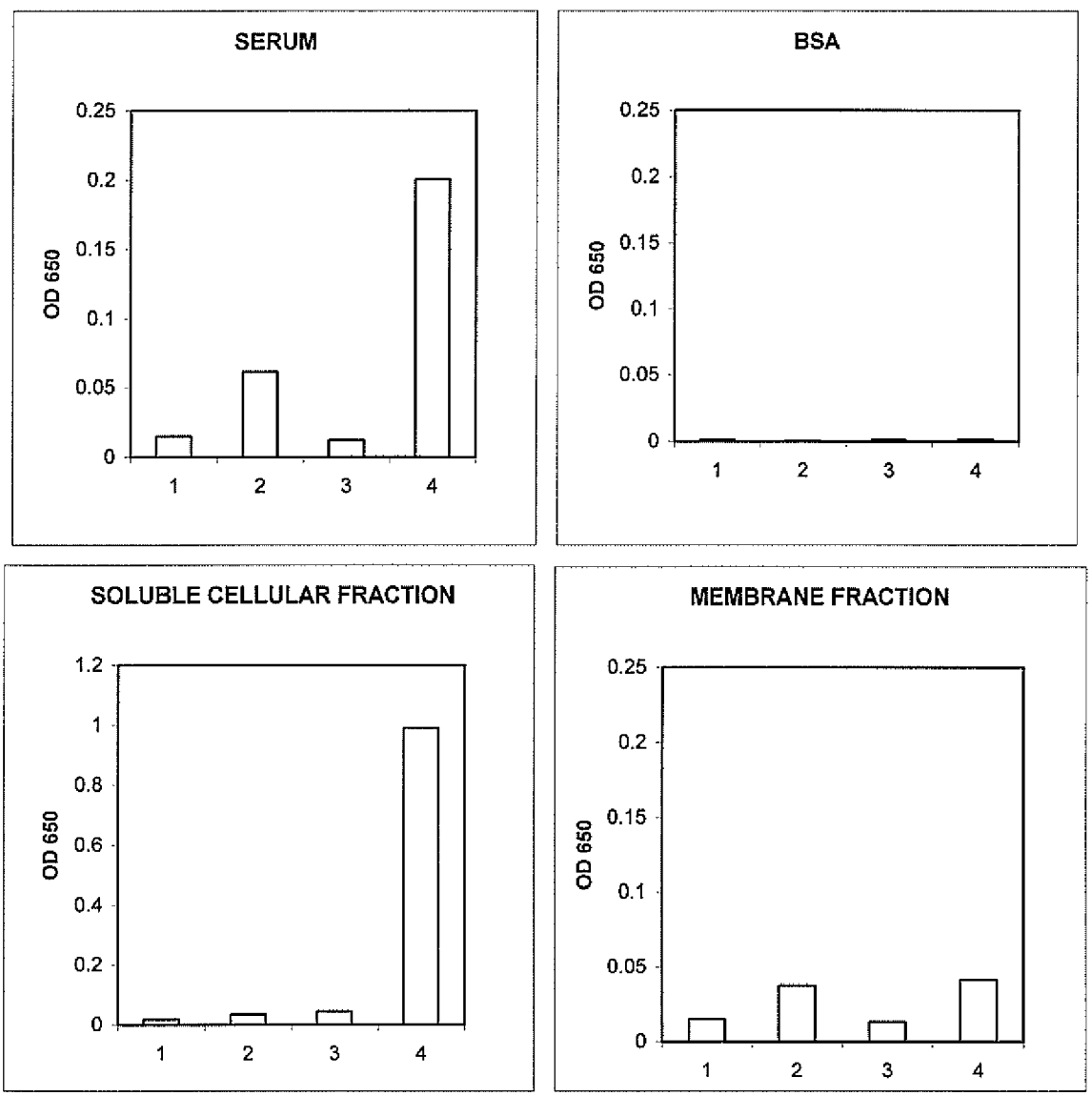
FIG. 1 shows the effect of pH and the use of surfactants on precipitation of proteins in different fractions of the blood: top left, serum; top right, bovine serum albumin; bottom left, soluble cell fraction and bottom right, membrane fraction.

In one embodiment, the present invention provides a cell permeabilization and stabilization reagent for preparing cells for flow cytometric analysis. The cell permeabilization and stabilization reagent comprises:

(a) N-acyl sarcosine or a salt thereof represented by the following molecular structure:

$R_1$—CO—N(CH$_3$)CH$_2$COOX$_1$ wherein $R_1$ is an alkyl or alkylene group having 8 to 18 carbon atoms, and $X_1$ is H, Na$^+$, or K$^+$;

(b) a pH adjusting agent to adjust pH of the reagent less than 7; and (c) an aqueous medium.

The reagent has a low ionic strength defined by a conductivity of less than 9.0 mS/cm.

The permeabilization and stabilization reagent is preferably slightly acidic, with a pH in a range from about 4 to about 6. More preferably, pH of the reagent is from about 4.6 to about 5.6. Preferably, the pH adjusting agent is a strong base or acid, therefore, a small quantity of the chemical can be used to adjust the pH within the desired range. In one preferred embodiment, N-acyl sarcosine free acid is used, and pyrrolidine, a strong organic base, or NaOH, a strong inorganic base, is used to adjust the pH between 4 and 6. If a N-acyl sarcosine salt is used, then a strong acid, such as HCl, can be used to adjust the pH.

It has been found that upon exposing the cells to the permeabilization and stabilization reagent, intracellular protein aggregation within the cellular membrane, which is necessary to conserve cell integrity after permeabilization, is more effective under a low ionic strength. For the purpose of the present invention, the ionic strength of the aqueous reagent composition is defined by conductivity of the reagent. When the ionic strength is too high, for example when the conductivity of the reagent is higher than 9 mS/cm, the reagent can no longer aggregate intracellular proteins, and the cells lose their integrity. Preferably, the permeabilization and stabilization reagent has a conductivity of less than 1.2 mS/cm. Since ionic compounds, such as salts, are the major contributors of the ionic strength of the reagent, it is preferred to have low salt concentration in the reagent.

Preferably, the cell permeabilization and stabilization reagent can further comprise bovine serum albumin (BSA), and glycerol. Bovine serum albumin enhances the solubility of the surfactant in the aqueous solution, and hence is beneficial for a long term use and storage of the reagent. It has been found that the combination of bovine serum albumin and glycerol further enhances permeability of the cellular membrane by the reagent.

N-acyl sarcosine, in a free acid form, and the salt thereof are commercially available. It is preferred to use the free acid form, which does not introduce metal ions into the reagent. N-acyl sarcosine in a free acid form is not water soluble. It can be pre-dissolved in an ethanol solution, and then added into the aqueous solution. As the pH of the reagent is adjusted between 4 and 6 by the pH adjusting agent, the N-acyl sarcosine is in the form of anion in the solution.

Suitable examples of N-acyl sarcosine include N-oleoyl sarcosine, N-stearoyl sarcosine, N-lauroyl sarcosine, N-myristoyl sarcosine, N-cocoyl sarcosine, and salts thereof. Preferably, the alkyl or alkylene group of $R_1$ has 12 carbon atoms. In one preferred embodiment, N-lauroyl sarcosine is used.

In further embodiment, the cell permeabilization and stabilization reagent can further comprise an anionic surfactant represented by following molecular structure:

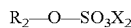

$$R_2—O—SO_3X_2$$

wherein $R_2$ is an alkyl or alkylene group having 8 to 18 carbon atoms; and $X_2$ is $Na^+$, $K^+$, $NH_4^+$, or $NH_2C(CH_2OH)_3$ (i.e., tris(hydroxymethyl)-aminomethane).

Preferably, the alkyl or alkylene group of $R_2$ of the anionic surfactant has 12 carbon atoms. Suitable examples include sodium, potassium, ammonium and tris(hydroxymethyl)aminomethane lauryl sulfates. In a preferred embodiment, tris(hydroxymethyl)aminomethane lauryl sulfate is used, which is referred to as Tris lauryl sulfate hereinafter.

N-acyl sarcosine or the salt thereof, or in combination with the alkyl or alkylene sulfate surfactant, is in a sufficient amount to enable the reagent permeating the cellular membrane of a cell for penetration of intracellular markers, while substantially preserving the cellular membrane and the cellular constituents for specific binding with their cellular markers for analysis by flow cytometry. It has been found that both surfactant concentrations can be in a range from about 0.01 mM to 100 mM, preferably 0.1 mM to 10 mM, and more preferably 1 mM to 5 mM. In one exemplary embodiment, 2.3 mM of N-lauroyl sarcosine was used. In another example, a mixture of 0.5 mM of Tris lauryl sulphate and 2.2 mM of N-lauroyl sarcosine was used.

Optionally, the permeabilization and stabilization can further comprise an organic osmolarity adjusting agent. Suitable examples of the osmolarity adjusting agent include, but are not limited to, ethylene glycol, dimethylsulphoxide, saccharide, or glycerol. Preferably, saccharide or glycerol is used. The saccharide can be a polysaccharide, such as a disaccharide, or a monosaccharide. Preferably, a monosaccharide, such as (D+) glucose, is used.

Furthermore, the permeabilization and stabilization can further comprise one or more preservatives. Suitable examples include antimicrobials and antioxidants, for extension of shelf life of the reagent. The preservative can be present in amount which does not interfere with the function of the reagent.

Example 1 shows three exemplary reagent compositions of the present invention.

It has been found that when mixed with cells, the cell permeabilization and stabilization reagent of the present invention effectively permeates the cellular membrane which enables penetration of intracellular markers into the cell for cellular analysis; and the reagent also causes intracellular protein precipitation or aggregation within the cellular membrane. At the same time, however, the reagent preserves the cellular constituents, such as intracellular and cell surface antigen sites, DNA and RNA molecules, and cytoskeleton elements.

For the purpose of the present invention, the term "cellular constituent" includes cellular components inside the cellular membrane, and on the surface of the cellular membrane such as cell surface antigen sites. While the term "intracellular constituent" refers to a cellular component inside the cellular membrane, which includes, but is not limited to, intracellular proteins, such as hemoglobin and hemoglobin variants inside erythrocytes, cytoskeleton elements, and DNA and RNA. The cytoskeleton elements include, but are not limited to, tubulin and spectrin.

The surfactant(s) in the concentration described above have the property of causing the aggregation of the polypeptides and proteins at a slightly acidic pH, which does not denature the intracellular antigen sites, and does not destroy the cellular membrane. In order to bring about the penetration and reaction of an antibody with an antigen site, it is preferred to introduce an antibody with an increased pH. It has been found that after treating the cells with the cell permeabilization and stabilization reagent, the cellular constituents are stable for a sufficient period of time to allow addition of a salt containing and buffered medium to cause an antibody to react with an intracellular antigen, prior to fixing the cell with a fixing agent. These properties are illustrated in detail hereafter in the examples.

It should be understood that the effect produced by the surfactant in the cell permeabilization and stabilization reagent of the present invention is substantially different from the effect produced by a surfactant typically used for preparing a blood sample, where the surfactant causes cell lysis. Under those conditions, the cellular membrane of erythrocytes is destroyed for releasing hemoglobin for hemoglobin measurement, or for the measurement of leukocytes.

In a further embodiment, the present invention provides a method of permeating cellular membrane and stabilizing cellular constituents of a cell using the reagent of the present invention for analysis of cellular constituents on a flow cytometric instrument.

More specifically, the method comprises the steps of mixing a sample containing cells with the cell permeabilization and stabilization reagent of the present invention to form a sample mixture; and incubating the sample mixture for a period of time sufficient to permeate cellular membrane, cause intracellular protein aggregation within the cellular membrane, and preserve cellular constituents for binding with cellular markers. The method further comprises the step of adding a cellular marker into the sample mixture and incubating the sample mixture for a second period of time to allow the cellular marker bind with the preserved cellular constituent. Optionally, the method can further comprise the step of adding a fixative into the sample mixture to fix the cells after the cellular marker binds with the cellular constituent. The sample mixture can then be introduced to a flow cytometric instrument for analysis of cellular constituent of interest.

The term of "cellular marker" used herein includes, but is not limited to, an antibody specific to an antigen site of an intracellular protein, a cell surface antigen site, or a cytoskeleton element; a nucleic acid dye and a nucleic acid probe specific to a DNA or a RNA molecule, such as an oligonucleotide probe. Preferably, the cellular marker is labelled with a fluorescent dye. Furthermore, the cellular marker specific to an intracellular constituent is also referred to as an intracellular marker.

It has been found that the incubation of the sample with the cell permeabilization and stabilization reagent can be from 5 seconds, preferably for about 5 minutes at room temperature. The second incubation after addition of the cellular marker can be from about 2 minutes, preferably about 15 minutes.

The cells to be analyzed using the cell permeabilization and stabilization reagent of the present invention can be tissue cells, on a microscope slide, or cells originating from cell lines in culture, or present in biological liquids, in particular blood cells and particularly erythrocytes or leukocytes. The cells to be analyzed can be situated in human tissue, on a microscope slide, or in suspension.

More particularly, the cell permeabilization and stabilization reagent of the present invention can be used in the field of hematology for the analysis of the cellular constituents of erythrocytes. More specifically, the reagent can be used in research and diagnosis of diseases related to different and aberrant forms of hemoglobin, for example, foetal hemorrhagia in pregnant women by the presence of foetal hemoglobin, or diabetes by the presence of glycolic hemoglobin. It may potentially be used for detection of infecting agents of erythrocytes, such as malaria.

Examples 2 to 4 illustrate the effect of pH and the surfactants in the permeabilization and stabilization reagent, with Composition C of Example 1.

FIG. 1 shows the effect of pH and the presence of surfactants in the Composition C of Example 1 on the precipitation of the serum components, the soluble cellular fraction (cytosol) and a membrane preparation as described in Example 2. In each preparation, with the exception of the bovine serum albumin, a synergistic effect between an acidic pH and the presence of the surfactants with respect to protein aggregation has been shown. In the cytosol sample, the synergistic effect is very strong, because of the presence of hemoglobin, with strong aggregation and precipitation upon reacting with the permeabilization reagent. In the membrane fraction, the synergy seems less strong, but the result is masked by the dissolution of the lipid parts of the membranes by the surfactant, which leads to underestimation of the OD 650 value in column 4.

FIGS. 2A thru 2J show the effect of pH and the presence of surfactants in the Composition C of Example 1 on the cell morphology preservation and the permeabilization of the erythrocyte by an antibody.

Figure 2A:
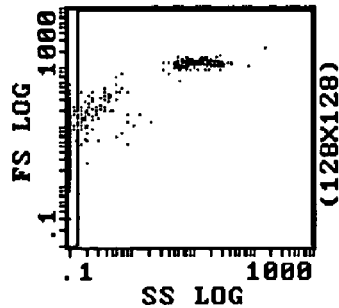
FIGS. 2A thru 2J show the effect of pH and the use of surfactants on the preservation and permeabilization of erythrocytes.
Figure 2B:
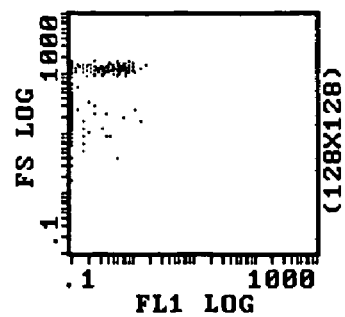

At pH 7.0 and in the absence of surfactant, the erythrocytes show as the upper population in FIG. 2A, well separated from the platelets and debris in the lower population. FIG. 2B shows that the erythrocytes have no permeability vis-à-vis an anti-tubulin-fluorescein N-isothiocyanate (FITC) antibody.

Figure 2C:
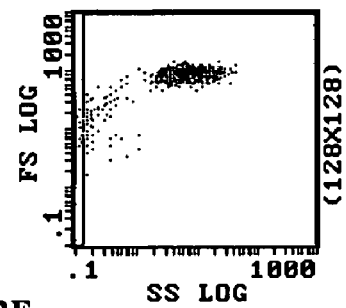
Figure 2D:
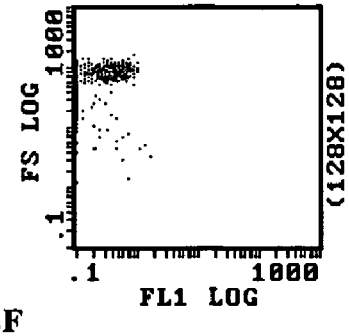
Figure 2E:
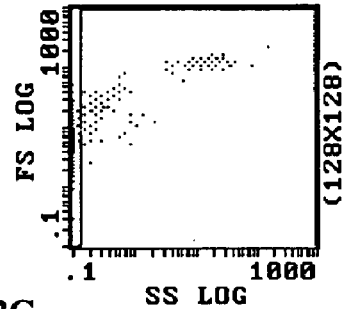
Figure 2F:
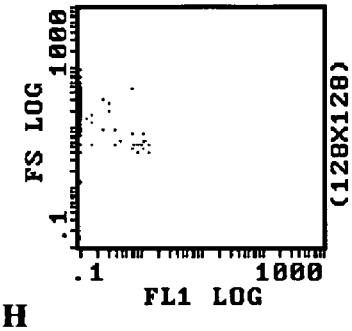

At pH 5.0 and in the absence of surfactant (FIGS. 2C and 2D), the morphology and permeability are about the same to the preceding conditions. On the other hand, FIGS. 2E and 2F show the destruction of the erythrocytes in the presence of surfactant at pH 7.0.

Figure 2G:
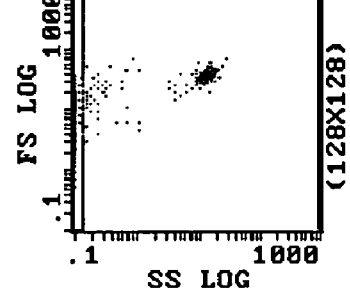
Figure 2H:
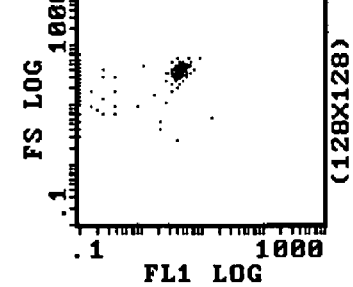
Figure 2I:
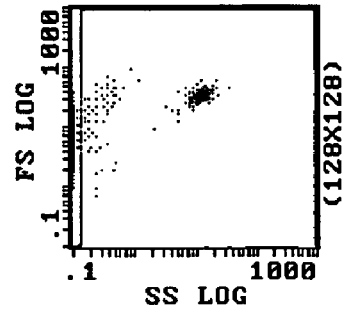
Figure 2J:
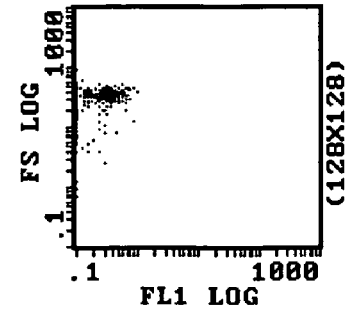

FIGS. 2G and 2H show that after incubation of blood with the Composition C of Example 1, the erythrocytes were well preserved. The cluster of cells shown in FIG. 2H clearly shows the binding of the cells with the anti-tubulin-FITC antibody and illustrates erythrocytes were permeabilized vis-à-vis the anti-tubulin-FITC antibody. FIGS. 2I and 2J show the blood treated with the Composition C of Example 1, but incubated with an isotype control antibody conjugated to FITC, which is non-specific for any known cellular constituent. FIG. 2J shows a very low or no binding of the cells with the control antibody, which confirms the specificity of the anti-tubulin-FITC antibody reaction.

Figure 3A:
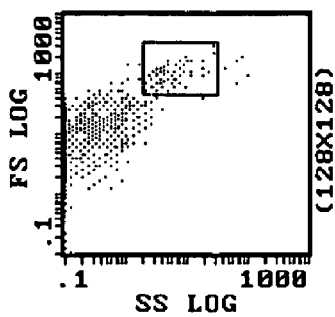
FIGS. 3A thru 3J show the effect of pH and the use of surfactants on the preservation and permeabilization of leukocytes.
Figure 3B:
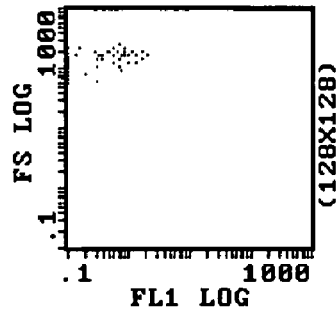

FIGS. 3A thru 3J show the effect of pH and surfactants on the preservation and permeability of the leukocytes. After separation of the red blood cells and the granulocytes, mononuclear peripheral cells were mixed with the permeabilization reagent at pH 7.0, without surfactant. FIG. 3A shows the lymphocyte population framed. The lower population is platelets and debris. Under the conditions described, the lymphocytes are not permeable to the anti-tubulin antibody, as shown in FIG. 3B.

Figure 3C:
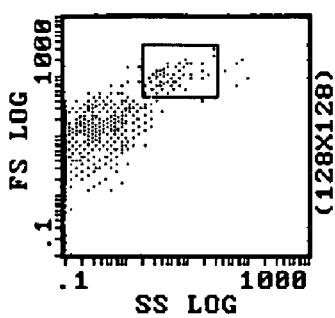
Figure 3D:
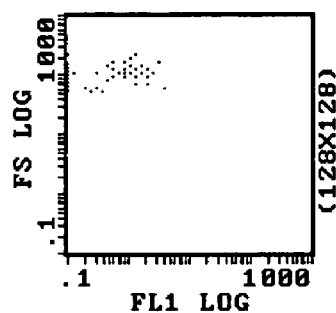

FIGS. 3C and 3D show results obtained using a permeabilization reagent of pH 5.0 without surfactant, which are similar to those observed in 3A and 3B. For FIGS. 3E and 3F, a permeabilization reagent is used at pH 7.0 and in the presence of surfactant. The destruction of the lymphocytes was observed.

Figure 3E:
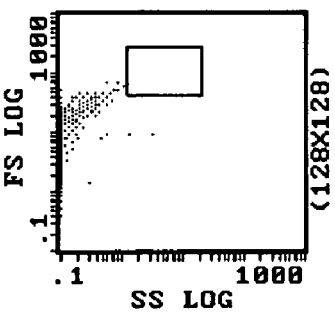
Figure 3F:
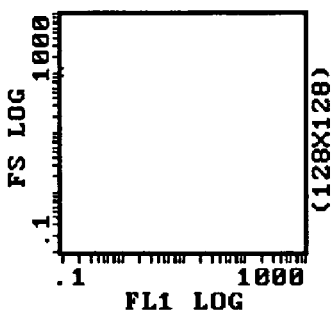
Figure 3G:
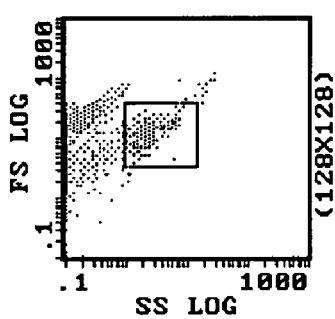
Figure 3H:
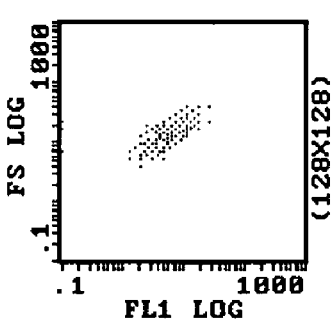
Figure 3I:
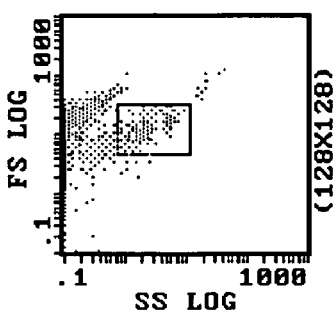
Figure 3J:
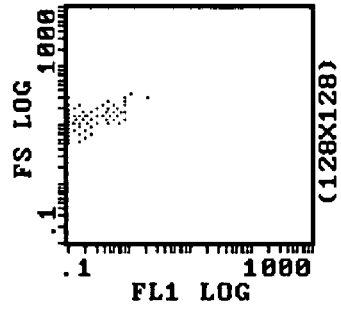

For FIGS. 3G and 3H, the Composition C of Example 1 was used, which had the surfactants and pH 5.0. The cells shown in FIG. 3H clearly illustrate permeabilization of the lymphocytes by the anti-tubulin-FITC antibody. FIGS. 3I and 3J show results obtained using a non-specific isotype control antibody. FIG. 3J shows a very low or no binding of the cells with the control antibody, which confirms the specificity of the anti-tubulin-FITC antibody reaction.

Example 5 illustrates a process of using the cell permeabilization and stabilization reagent for analysis of foetal hemoglobin.

Figure 4A:
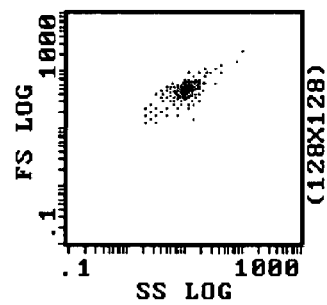
FIGS. 4A thru 4F show the results of detection of F cells and foetal cells in the blood by use of the foetal hemoglobin antigens (HbF) and i.
Figure 4B:
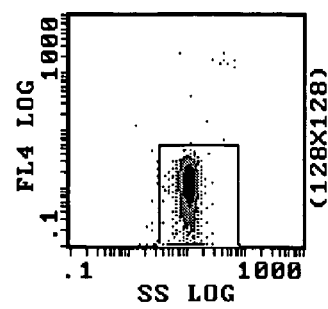
Figure 4C:
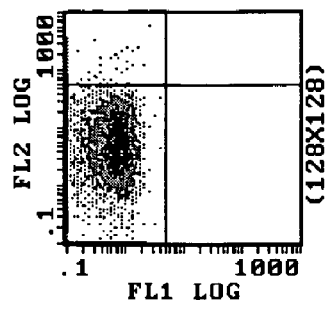

FIGS. 4A thru 4F show identification of the foetal erythrocytes by intracellular marking by anti-HbF-FITC and by extracellular marking by anti-i-phycoerythrin (PE). More specifically, the individual scattergrams are:

FIGS. 4A, 4B and 4C: marking in the absence of calcium.

Figure 4D:
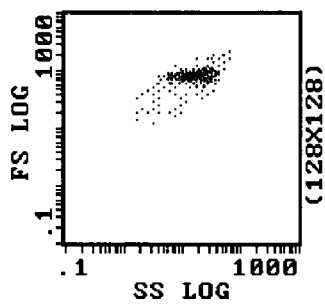
Figure 4E:
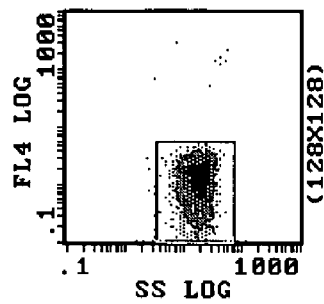
Figure 4F:
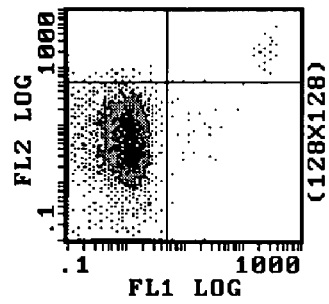

FIGS. 4D, 4E and 4F: marking in the presence of 1 mM of calcium.

FIGS. 4A and 4D: scattergrams of the blood constituents. The platelets and debris have been eliminated from the scattergrams by installation of a threshold.

FIGS. 4B and 4E: populations of erythrocytes gated in the frame after elimination of the leukocytes by CD 45-PC 5 in the FL4.

FIGS. 4C and 4F show the adult erythrocytes (HbF−,i+) in quadrant 3 (bottom left), the foetal erythrocytes (HbF+,i+) in quadrant 2 (top right) and the F cells (HbF+,i−) in quadrant 4 (bottom right).

Example 6 illustrates detection of alpha tubulin and glycated hemoglobin (HbA1c) by fluorescence on a flow cytometer using the cell permeabilization and stabilization reagent of the present invention.

It has been illustrated that the permeabilization reagent of the present invention is able to permeate cellular membrane, cause precipitation of intracellular proteins, and while preserve the cellular constituent for specific binding to its cellular marker for flow cytometric analysis using light scatter and fluorescence.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Permeabilization Reagent Compositions

Composition A

Following permeabilization and stabilization reagent composition was prepared.

| | |
|---|---|
| N-lauroyl sarcosine | 2.3 mM |
| Pyrrolidine and HCl | quantity to adjust pH to 5.3 |

More specifically, a stock solution of N-lauroyl sarcosine was made first. 1.0 g of N-lauroyl sarcosine (Fluka) was pre-dissolved in 1.5 ml of ethanol (96%). 180 µl of pyrrolidine (Aldrich) was added into 95 ml of deionized water. Then the N-lauroyl sarcosine/ethanol solution was added into the pyrrolidine solution; the pH was adjusted to 5.6 by pyrrolidine or HCl, and the volume was adjusted to 100 ml with deionized water to form the stock solution. The total volume of the reagent is adjusted to 100 ml with deionized water. The permeabilization and stabilization reagent composition was prepared by diluting 6.25 ml of the stock solution with deionized water to 100 ml and adjusting pH to 5.3 with pyrrolidine or HCl. The Composition A had a conductivity of 0.1 mS/cm.

Composition B

Following permeabilization reagent composition was prepared by dissolving each compound in deionized water.

| | |
|---|---|
| N-lauroyl sarcosine | 2.3 mM |
| Bovine serum albumin | 1.1 g/l |
| Glycerol | 1.08 M |
| Pyrrolidine and HCl | quantity to adjust pH to 5.3 |

The reagent composition had a conductivity of 0.25 mS/cm. N-lauroyl sarcosine was added as the stock solution, as described above.

Composition C

Following permeabilization reagent composition was prepared by dissolving each compound in deionized water.

| | |
|---|---|
| N-lauroyl sarcosine | 2.2 mM |
| Tris lauryl sulphate | 0.5 mM |
| Succinic acid | 4 mM |
| Boric acid | 40 mM |
| D (+) glucose | 166 mM |
| Pyrrolidine and HCl | quantity to adjust pH to 5.0 |

The reagent composition had a conductivity of 0.5 mS/cm. N-lauroyl sarcosine was added as the stock solution, as described above.

EXAMPLE 2

Effect of pH, Surfactants and the Combination of pH and Surfactants on the Precipitation of Different Components of the Erythrocytes A quantity of blood, treated with 0.7 mM of ethylenediamine tetraacetic acid (EDTA) as anticoagulant, was used to prepare blood serum. Another quantity of the EDTA treated blood was washed with phosphate buffered saline (PBS), and diluted with nine volumes of water to obtain a cell lysate. The cell lysate was subjected to centrifugation at 2000 g for 15 minutes to separate the soluble cell fraction and the membrane fraction. The pellet containing the membrane fraction was mixed with a volume of water, which contains 5% in volume of the soluble cell fraction.

Precipitation of the serum, soluble cell fraction, membrane fraction, as well as bovine serum albumin as a control, was monitored after mixing with the Composition C of Example 1, and with the following modified reagents:

1. Modified Reagent 1: Composition C of Example 1 without addition of the surfactants (Tris lauryl sulphate and N-lauroyl sarcosine), having a pH of 7.0.
2. Modified Reagent 2: Composition C of Example 1 without addition of the surfactants (Tris lauryl sulphate and N-lauroyl sarcosine), having a pH of 5.0.
3. Modified Reagent 3: Composition C of Example 1, having a pH of 7.0.
4. Permeabilization Reagent 4: Composition C of Example 1 as described (pH 5.0).

Sample mixtures were produced by mixing 2 ml of a specific reagent described above with one of the following four components:
  0.01 ml of serum (A),
  0.01 ml of a preparation of bovine albumin at 15% weight/volume (B),
  0.1 ml of soluble cell fraction (C), and
  0.1 ml of membrane fraction (D).

In order to determine the precipitation of the proteins one hour after preparation of the sample mixtures, the optical density of the sample mixtures was measured at 650 nm, the wavelength at which hemoglobin, the principal constituent of the fractions, does not absorb.

FIG. 1 shows the effect of pH and the surfactants in the reagent on the precipitation of the cellular components in: serum; a preparation of bovine serum albumin (BSA) at 15% weight/volume; soluble cell fraction (cytosol); and membrane fraction. The bar graph for each of the above referenced cellular components shows the results, from the left to right, obtained using the Modified Reagents 1 to 3 and the Permeabilization Reagent 4.

FIG. 1 shows that only the Permeabilization Reagent 4, which contained the surfactant with a low pH as described above, led to aggregation and precipitation of proteins.

EXAMPLE 3

Effect of pH, Surfactants and of a Combination of Acidic pH and Surfactants on the Penetration of an Antibody into the Erythrocytes 0.01 ml of a whole blood was mixed with 100 µl of a saline solution and then with 2 ml of each permeabilization reagent variant as described above in Example 2. After incubation for 5 minutes, 50 µl of each mixture was added to 50 µl of a PBS solution which contained 0.2% (w/v) of bovine serum albumin and a monoclonal antibody conjugated to FITC and directed against alpha tubulin (Beckman Coulter Inc. Miami, USA). Alpha tubulin is a molecule expressed exclusively inside the cell. After incubation for 15 minutes, the mixture was mixed with 1 ml of PBS containing 0.5% of formaldehyde, to stop the reaction and fix the cells, which formed the sample mixture for analysis.

The sample mixtures were analyzed on an XL™ flow cytometer (Beckman Coulter Miami, USA). The integrity of the cells was analyzed by the forward scatter and the side scatter. The permeability of the cells was analyzed by the fluorescence of the FITC antibodies. The results are shown in FIGS. 2A thru 2J. More specifically, the individual scattergrams are:

FIGS. 2A and 2B: pre-incubation of blood with Modified Reagent 1.
FIGS. 2C and 2D: pre-incubation of blood with Modified Reagent 2.
FIGS. 2E and 2F: pre-incubation of blood with Modified Reagent 3.
FIGS. 2G and 2H: pre-incubation of blood with the Permeabilization Reagent 4.
FIGS. 2I and 2J: pre-incubation with the Permeabilization Reagent 4, reacting with an isotype control antibody conjugated to FITC.

Wherein FS is the forward light scatter; SS is the side scatter; FL1, FL2 and FL4 are the fluorescence signals measured at 525 nm, 575 nm, and 675 nm, respectively.

The control antibody was isotype antibody conjugated to FITC, which is non-specific for any known cellular constituent.

It was observed that only the Permeabilization Reagent 4 which contained the surfactants and had a low pH, had the effect of permeabilization and preservation of the erythrocytes.

EXAMPLE 4

Effect of pH, Surfactants and Combination of pH and Surfactants on the Penetration of an Antibody into the Leukocytes Mononuclear leukocytes were prepared from peripheral blood in the presence of EDTA using a Ficoll according to the method of A. Boyem (1968, Scand. J. Clin. Lab. Invest., 21 Suppl. 97). 10 million cells were mixed with 100 µl of a saline solution and then mixed with 2 ml of each permeabilization reagent variant as described in Example 2. Incubation of the cells and the intracellular marking with an anti-tubulin-FITC antibody were carried out as described in Example 3. The results are shown in FIGS. 3A thru 3J. More specifically, the individual scattergrams are:

FIGS. 3A, 3B: pre-incubation of cells with Modified Reagent 1.
FIGS. 3C, 3D: pre-incubation of cells with Modified Reagent 2.
FIGS. 3E, 3F: pre-incubation of cells with Modified Reagent 3.
FIGS. 3G, 3H: pre-incubation of cells with Permeabilization Reagent 4.
FIGS. 3I, 3J: pre-incubation of cells with Permeabilization Reagent 4, reacting with an isotype control antibody conjugated to FITC.

It was observed that only the Permeabilization Reagent 4 which contained surfactants and had a low pH, had a permeabilization and preservation effect on the leukocytes.

EXAMPLE 5

Use of the Permeabilization Reagents for the Detection of Foetal Erythrocytes Based on Foetal Antigens Inside and at the Surface of the Cell A mixture of 99% (v/v) of a normal blood and 1% (v/v) umbilical cord blood was used for the detection of foetal erythrocytes. 100 µl of a saline solution and then 1 ml of the Composition C were added to 5 µl of the blood mixture. After incubation for 10 minutes, 50 µl of the sample mixture were added to two tubes which contained:

Tube A contained 50 µl of a PBS solution containing 0.2% (w/v) of bovine serum albumin and a mixture of the following antibodies:
- an anti-foetal hemoglobin (HbF) monoclonal antibody conjugated to FITC (French Patent No. 98 09006);
- an anti-foetal blood group i monoclonal antibody conjugated to phycoerythrin (French Patent No. No 98 09006); and
- an anti-CD45-PC5 monoclonal antibody (Beckman Coulter Inc. Marseille France).

Tube B contained the same content of the Tube A, in addition, 10 µl of 10 mM $CaCl_2$ was added.

Tube A served as a negative control for the reaction with HbF, since the reaction depended on the presence of calcium ($Ca^{2+}$) ions.

The mixtures were analyzed an XL flow cytometer (Beckman Coulter Miami, USA). The integrity of the cells was analyzed by the forward scatter and the side scatter. CD45 was used to exclude the leukocytes from the analysis. The foetal erythrocytes were detected by the fluorescence of the antibodies. The results are given in FIGS. 4A thru 4F. FIGS. 4A to 4C show the results obtained from Tube A, and FIGS. 4D to 4E show the results obtained from Tube B.

It was observed that in FIGS. 4C and 4F, the adult erythrocytes (HbF−,i+) were situated in quadrant 3 (bottom left), the foetal erythrocytes (HbF+,i+) were situated in quadrant 2 (top right) and the F cells (HbF+,i−) were situated in quadrant 4 (bottom right).

It was noted that in the absence of calcium ions, there were no foetal erythrocytes in quadrant 2 of FIG. 4C. Therefore, the erythrocytes were permeable to the conjugated antibodies and the interaction between the HbF antigen and the anti-HbF antibody depended on calcium ions. Apparently, the HbF antigen was preserved in its natural state, which was demonstrated by the preservation of the calcium-dependency of the interaction between the HbF and the antibody, after incubation of the erythrocytes with the permeabilization reagent of the present invention.

EXAMPLE 6

Detection of Alpha Tubulin and HbA1C in the Erythrocytes 0.01 ml of a whole blood was mixed with 100 µl of a saline solution and then with 2 ml of Composition B of Example 1. After incubation for 5 minutes, 50 µl of the mixture was added to 50 µl of PBS containing a monoclonal antibody conjugated to FITC and directed against alpha tubulin (anti-tubulin-FITC antibody, Beckman Coulter Inc. Miami, USA), or containing a monoclonal antibody directed against HbA1c and conjugated to FITC (anti-HbA1c-FITC antibody), which was prepared according to the process of Knowles et al described in U.S. Pat. No. 4,727,036. After incubation for 15 minutes, the mixture was mixed with 1 ml of PBS containing 0.5% of formaldehyde, to stop the reaction and fix the cells, which formed the sample mixture for analysis.

Figure 5A:
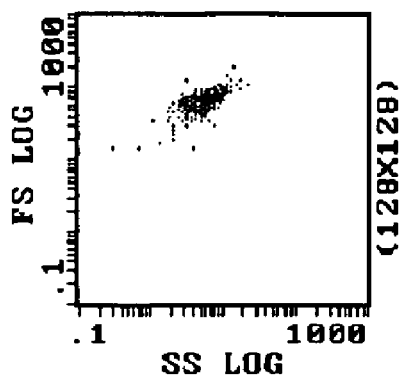
FIGS. 5A thru 5F show the results of detection of alpha tubulin and glycated hemoglobin (HbA1c) in the blood by use of the alpha tubulin and HbA1c antigens, respectively.
Figure 5B:
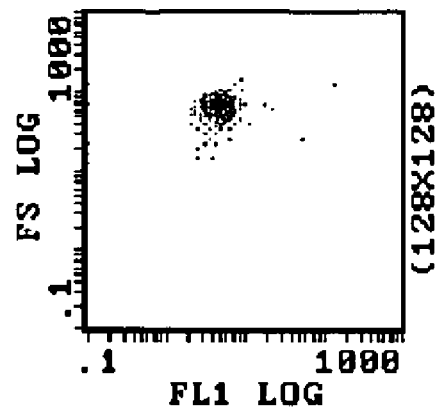

The sample mixtures were analyzed on an XL flow cytometer (Beckman Coulter Miami, USA). The integrity of the cells was analyzed by the forward scatter and the side scatter. The permeability of the cells was analyzed by the fluorescence of the FITC antibodies. The results are shown in FIGS. 5A thru 5F. More specifically, the individual scattergrams are:

FIGS. 5A and 5B: reaction with anti-tubulin-FITC antibody.

Figure 5C:
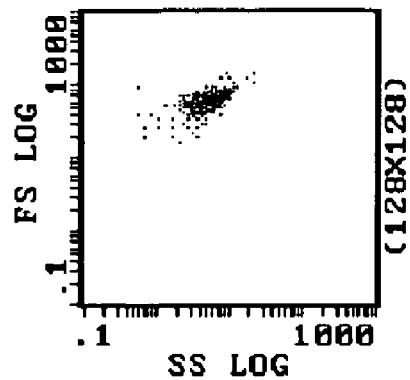
Figure 5D:
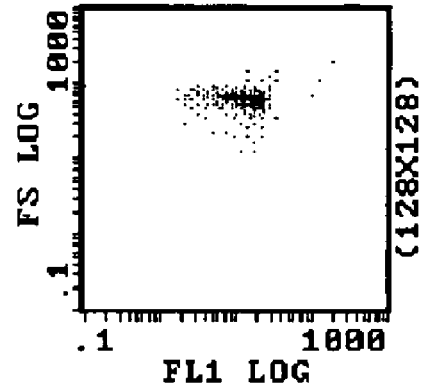

FIGS. 5C and 5D: reaction with anti-HbA1c-FITC antibody.

Figure 5E:
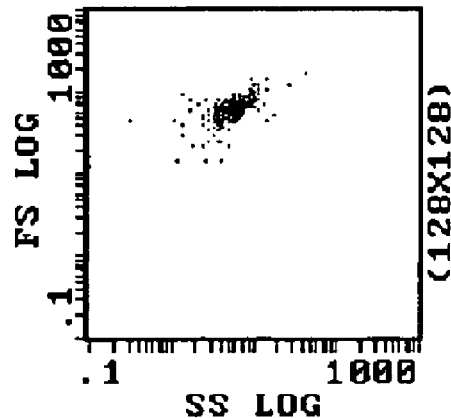
Figure 5F:
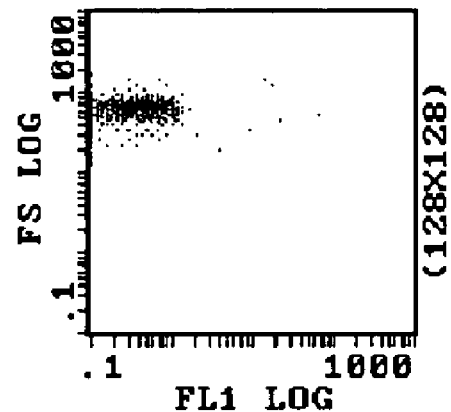

FIGS. 5E and 5F: reaction with an isotype control antibody conjugated to FITC.

The control antibody was isotype antibody conjugated to FITC, which is non-specific for any known cellular constituent.

As shown, the erythrocytes were permeable to both the anti-tubulin-FITC antibody, and the anti-HbA1c-FITC antibody, which enabled the detection of alpha tubulin and HbA1c in the erythrocytes by fluorescence on the flow cytometer.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A cell permeabilization and stabilization reagent comprising an aqueous solution of:
    (a) N-acyl sarcosine or a salt thereof represented by the following molecular structure:

$$R_1-CO-N(CH_3)CH_2COOX_1$$

wherein $R_1$ is an alkyl or alkylene group having 8 to 18 carbon atoms, and $X_1$ is H, Na$^+$, or K$^+$;
    (b) bovine serum albumin; and
    (c) a saccharide or glycerol;
    said reagent having a pH less than 7 and having a low ionic strength defined by a conductivity of less than 1.2 mS/cm.

2. The reagent of claim 1, wherein said pH is in a range from about 4 to about 6.

3. The reagent of claim 1, wherein said N-acyl sarcosine is N-lauroyl sarcosine.

4. The reagent of claim 3, wherein said N-lauroyl sarcosine is in a concentration range from about 0.1 mM to about 10 mM.

5. The reagent of claim 1, wherein said saccharide is disaccharide, or monosaccharide.

6. A sample mixture composition comprising:
    (a) a whole blood; and
    (b) a cell permeabilization and stabilization reagent comprising an aqueous solution of 0.1 mM to 10 mM of N-acyl sarcosine or a salt thereof represented by the following molecular structure:

$$R_1-CO-N(CH_3)CH_2COOX_1$$

wherein R1 is an alkyl or alkylene group having 8 to 18 carbon atoms, and $X_1$ is H, Na$^+$, or K$^+$;
    said reagent having a pH between 4 and 6 and a conductivity less than 1.2 mS/cm; and
    wherein the cellular membrane of blood cells in said whole blood is permeated and intracellular proteins of said blood cells are caused to aggregate by said reagent, while said blood cells are preserved for cellular analysis.

7. The sample mixture composition of claim 6 further comprising a monoclonal antibody.

8. The sample mixture composition of claim 7 further comprising a fixative.

9. A cell permeabilization and stabilization reagent comprising an aqueous solution of:
    (a) 0.1 mM to 10 mM of N-acyl sarcosine or a salt thereof represented by the following molecular structure:

$$R_1-CO-N(CH_3)CH_2COOX_1$$

wherein R1 is an alkyl or alkylene group having 8 to 18 carbon atoms, and $X_1$ is H, Na$^+$, or K$^+$; and
    (b) saccharide or glycerol;
    said reagent having a pH less than 7 and a low ionic strength defined by a conductivity of less than 1.2 mS/cm; wherein said reagent enables permeation of the cellular membrane and causes aggregation of intracellular proteins of blood cells while preserving said blood cells for cellular analysis.

10. The reagent of claim 9, wherein said pH is in a range from about 4 to about 6.

11. The reagent of claim 9, wherein said N-acyl sarcosine is N-lauroyl sarcosine.

12. The reagent of claim 9, wherein said saccharide is disaccharide, or monosaccharide.

* * * * *